United States Patent
Berend et al.

(10) Patent No.: US 9,549,742 B2
(45) Date of Patent: Jan. 24, 2017

(54) DEVICES AND METHODS FOR KNEE ARTHROPLASTY

(71) Applicant: OrthAlign, Inc., Aliso Viejo, CA (US)

(72) Inventors: Michael Berend, Indianapolis, IN (US); Jonathan Nielsen, Aliso Viejo, CA (US); Nicholas van der Walt, Laguna Hills, CA (US); Scott Richard Small, Terre Haute, IN (US)

(73) Assignee: OrthAlign, Inc., Aliso Viejo, CA (US)

( * ) Notice: Subject to any disclaimer, the term of this patent is extended or adjusted under 35 U.S.C. 154(b) by 0 days.

(21) Appl. No.: 14/401,274

(22) PCT Filed: May 17, 2013

(86) PCT No.: PCT/US2013/041556
§ 371 (c)(1),
(2) Date: Nov. 14, 2014

(87) PCT Pub. No.: WO2013/173700
PCT Pub. Date: Nov. 21, 2013

(65) Prior Publication Data
US 2015/0127009 A1 May 7, 2015

Related U.S. Application Data

(60) Provisional application No. 61/648,762, filed on May 18, 2012.

(51) Int. Cl.
*A61B 17/58* (2006.01)
*A61B 17/60* (2006.01)
(Continued)

(52) U.S. Cl.
CPC ........... *A61B 17/155* (2013.01); *A61B 17/157* (2013.01)

(58) Field of Classification Search
None
See application file for complete search history.

(56) References Cited

U.S. PATENT DOCUMENTS 3,174,080 A 3/1965 Scott
3,670,324 A 6/1972 Trevor, 3rd
(Continued)

FOREIGN PATENT DOCUMENTS

CA 2241359 12/1999
CA 2 594 874 7/2006
(Continued)

OTHER PUBLICATIONS

Extended European Search Report issue in European Patent Application No. 13790292.0, dated Oct. 28, 2015, in 7 pages.
(Continued)

*Primary Examiner* — Sameh Boles
(74) *Attorney, Agent, or Firm* — Knobbe, Martens, Olson & Bear, LLP

(57) ABSTRACT

The present invention provides, in certain embodiments, a device for positioning and orienting the femoral cutting block. The present invention also provides a device for setting rotation of sagittal resection for unicompartmental knee arthroplasty. The present invention further provides methods for setting the rotation of the tibial implant by kinematic measurements.

19 Claims, 10 Drawing Sheets

(51) Int. Cl.
*A61F 2/00* (2006.01)
*A61B 17/15* (2006.01)

(56) References Cited

U.S. PATENT DOCUMENTS

| | | |
|---|---|---|
| 4,349,018 A | 9/1982 | Chambers |
| 4,436,099 A | 3/1984 | Raftopoulos |
| 4,459,985 A | 7/1984 | McKay et al. |
| 4,475,549 A | 10/1984 | Oh |
| 4,501,266 A | 2/1985 | McDaniel |
| 4,509,393 A | 4/1985 | Castiglione |
| 4,518,855 A | 5/1985 | Malak |
| 4,524,766 A | 6/1985 | Petersen |
| 4,529,348 A | 7/1985 | Johnson et al. |
| 4,567,885 A | 2/1986 | Androphy |
| 4,567,886 A | 2/1986 | Petersen |
| 4,621,630 A | 11/1986 | Kenna |
| 4,646,729 A | 3/1987 | Kenna |
| 4,716,894 A | 1/1988 | Lazzeri et al. |
| 4,718,078 A | 1/1988 | Bleidorn et al. |
| 4,738,253 A | 4/1988 | Buechel et al. |
| 4,759,350 A | 7/1988 | Dunn et al. |
| 4,823,807 A | 4/1989 | Russell et al. |
| 4,938,762 A | 7/1990 | Wehrli |
| 4,944,760 A | 7/1990 | Kenna |
| 4,945,799 A | 8/1990 | Knetzer |
| 4,952,213 A | 8/1990 | Bowman et al. |
| 5,002,547 A | 3/1991 | Poggie et al. |
| 5,053,037 A | 10/1991 | Lackey |
| 5,065,612 A | 11/1991 | Ooka et al. |
| 5,122,146 A | 6/1992 | Chapman et al. |
| 5,129,908 A | 7/1992 | Petersen |
| 5,213,112 A | 5/1993 | Niwa et al. |
| 5,249,581 A | 10/1993 | Horbal et al. |
| 5,251,127 A | 10/1993 | Raab |
| 5,279,309 A | 1/1994 | Taylor et al. |
| 5,296,855 A | 3/1994 | Matsuzaki et al. |
| 5,306,276 A | 4/1994 | Johnson et al. |
| 5,320,625 A | 6/1994 | Bertin |
| 5,324,293 A | 6/1994 | Rehmann |
| 5,325,029 A | 6/1994 | Janecke et al. |
| 5,329,933 A | 7/1994 | Graf |
| 5,342,367 A | 8/1994 | Ferrante et al. |
| 5,343,391 A | 8/1994 | Mushabac |
| 5,358,526 A | 10/1994 | Tornier |
| 5,374,275 A | 12/1994 | Bradley et al. |
| 5,376,093 A | 12/1994 | Newman |
| 5,395,377 A | 3/1995 | Petersen et al. |
| 5,417,694 A | 5/1995 | Marik et al. |
| 5,423,827 A | 6/1995 | Mumme et al. |
| 5,431,653 A | 7/1995 | Callaway |
| 5,458,645 A | 10/1995 | Bertin |
| 5,462,548 A | 10/1995 | Pappas et al. |
| 5,468,244 A | 11/1995 | Attfield et al. |
| 5,470,354 A | 11/1995 | Hershberger et al. |
| 5,474,088 A | 12/1995 | Zaharkin et al. |
| 5,486,177 A | 1/1996 | Mumme et al. |
| 5,490,854 A | 2/1996 | Fisher et al. |
| 5,514,143 A | 5/1996 | Bonutti et al. |
| 5,529,070 A | 6/1996 | Augustine et al. |
| 5,540,693 A | 7/1996 | Fisher |
| 5,540,696 A | 7/1996 | Booth, Jr. et al. |
| 5,540,697 A | 7/1996 | Rehmann et al. |
| 5,553,198 A | 9/1996 | Wang et al. |
| 5,576,727 A | 11/1996 | Rosenberg et al. |
| 5,584,837 A | 12/1996 | Petersen |
| 5,597,379 A | 1/1997 | Haines et al. |
| 5,611,353 A | 3/1997 | Dance et al. |
| 5,624,444 A | 4/1997 | Wixon et al. |
| 5,628,750 A | 5/1997 | Whitlock et al. |
| 5,645,077 A | 7/1997 | Foxlin |
| 5,653,764 A | 8/1997 | Murphy |
| 5,681,316 A | 10/1997 | DeOrio et al. |
| 5,683,398 A | 11/1997 | Carls et al. |
| 5,688,282 A | 11/1997 | Baron et al. |
| 5,720,752 A | 2/1998 | Elliott et al. |
| 5,724,264 A | 3/1998 | Rosenberg et al. |
| 5,733,292 A | 3/1998 | Gustilo et al. |
| 5,748,767 A | 5/1998 | Raab |
| 5,769,861 A | 6/1998 | Vilsmeier |
| 5,776,137 A | 7/1998 | Katz |
| 5,788,700 A | 8/1998 | Morawa et al. |
| 5,817,097 A | 10/1998 | Howard et al. |
| 5,824,085 A | 10/1998 | Sahay et al. |
| 5,840,047 A | 11/1998 | Stedham |
| 5,880,714 A | 3/1999 | Rosenberg et al. |
| 5,916,219 A | 6/1999 | Matsuno et al. |
| 5,919,149 A | 7/1999 | Allen |
| 5,935,086 A | 8/1999 | Beacon et al. |
| 5,976,156 A | 11/1999 | Taylor et al. |
| 6,022,377 A | 2/2000 | Nuelle et al. |
| 6,027,507 A | 2/2000 | Anderson et al. |
| 6,036,696 A | 3/2000 | Lambrecht et al. |
| 6,056,756 A | 5/2000 | Eng et al. |
| 6,090,114 A | 7/2000 | Matsuno et al. |
| 6,094,019 A | 7/2000 | Saiki |
| 6,096,043 A | 8/2000 | Techiera et al. |
| 6,120,509 A | 9/2000 | Wheeler |
| 6,122,538 A | 9/2000 | Sliwa, Jr. et al. |
| 6,126,608 A | 10/2000 | Kemme et al. |
| 6,162,191 A | 12/2000 | Foxlin |
| 6,167,292 A | 12/2000 | Badano et al. |
| 6,171,310 B1 | 1/2001 | Giordano |
| 6,195,615 B1 | 2/2001 | Lysen |
| 6,197,032 B1 | 3/2001 | Lawes et al. |
| 6,214,013 B1 | 4/2001 | Lambrech et al. |
| 6,214,014 B1 | 4/2001 | McGann |
| 6,216,029 B1 | 4/2001 | Paltieli |
| 6,246,898 B1 | 6/2001 | Vesely et al. |
| 6,258,095 B1 | 7/2001 | Lombardo et al. |
| 6,261,247 B1 | 7/2001 | Ishikawa et al. |
| 6,348,058 B1 | 2/2002 | Melken et al. |
| 6,354,011 B1 | 3/2002 | Albrecht |
| 6,361,506 B1 | 3/2002 | Saenger et al. |
| 6,361,507 B1 | 3/2002 | Foxlin |
| 6,361,508 B1 | 3/2002 | Johnson et al. |
| 6,381,485 B1 | 4/2002 | Hunter et al. |
| 6,395,005 B1 | 5/2002 | Lovell |
| 6,447,448 B1 | 9/2002 | Ishikawa et al. |
| 6,470,207 B1 | 10/2002 | Simon et al. |
| 6,471,637 B1 | 10/2002 | Green et al. |
| 6,473,635 B1 | 10/2002 | Rasche |
| 6,477,400 B1 | 11/2002 | Barrick |
| 6,477,421 B1 | 11/2002 | Andersen et al. |
| 6,478,799 B1 | 11/2002 | Williamson |
| 6,488,713 B1 | 12/2002 | Hershnerger |
| 6,499,488 B1 | 12/2002 | Hunter et al. |
| 6,514,259 B2 | 2/2003 | Picard et al. |
| 6,527,443 B1 | 3/2003 | Vilsmeier |
| 6,551,325 B2 | 4/2003 | Neubauer et al. |
| 6,585,666 B2 | 7/2003 | Suh et al. |
| 6,595,997 B2 | 7/2003 | Axelson, Jr. et al. |
| 6,595,999 B2 | 7/2003 | Marchione et al. |
| 6,607,487 B2 | 8/2003 | Chang et al. |
| 6,640,128 B2 | 10/2003 | Vilsmeier et al. |
| 6,679,916 B1 | 1/2004 | Frankie et al. |
| 6,685,711 B2 | 2/2004 | Axelson et al. |
| 6,711,431 B2 | 3/2004 | Sarin et al. |
| 6,712,824 B2 | 3/2004 | Millard et al. |
| 6,715,213 B2 | 4/2004 | Richter |
| 6,725,080 B2 | 4/2004 | Melkent et al. |
| 6,725,173 B2 | 4/2004 | An |
| 6,743,235 B2 | 6/2004 | Rao |
| 6,770,078 B2 | 8/2004 | Bonutti |
| 6,786,877 B2 | 9/2004 | Foxlin |
| 6,820,025 B2 | 11/2004 | Bachmann et al. |
| 6,827,723 B2 | 12/2004 | Carson |
| 6,917,827 B2 | 7/2005 | Kienzle, III |
| 6,923,817 B2 | 8/2005 | Carson et al. |
| 6,928,742 B2 | 8/2005 | Broers et al. |
| 6,947,783 B2 | 9/2005 | Immerz |
| 6,986,181 B2 | 1/2006 | Murphy et al. |
| 6,997,882 B1 | 2/2006 | Parker et al. |
| 7,007,699 B2 | 3/2006 | Martinelli et al. |

(56) References Cited

U.S. PATENT DOCUMENTS

| | | |
|---|---|---|
| 7,021,140 B2 | 4/2006 | Perkins |
| 7,027,477 B2 | 4/2006 | Sutter et al. |
| 7,037,310 B2 | 5/2006 | Murphy |
| 7,048,741 B2 | 5/2006 | Swanson |
| 7,089,148 B1 | 8/2006 | Bachmann et al. |
| 7,094,241 B2 | 8/2006 | Hodorek et al. |
| 7,104,998 B2 | 9/2006 | Yoon et al. |
| 7,105,028 B2 | 9/2006 | Murphy |
| 7,194,295 B2 | 3/2007 | Vilsmeier |
| 7,209,776 B2 | 4/2007 | Leitner |
| 7,219,033 B2 | 5/2007 | Kolen |
| 7,273,500 B2 | 9/2007 | Williamson |
| 7,331,932 B2 | 2/2008 | Leitner |
| 7,344,541 B2 | 3/2008 | Haines et al. |
| 7,392,076 B2 | 6/2008 | de La Barrera |
| 7,396,357 B2 | 7/2008 | Tornier et al. |
| 7,412,897 B2 | 8/2008 | Crottet et al. |
| 7,442,196 B2 | 10/2008 | Fisher et al. |
| 7,444,178 B2 | 10/2008 | Goldbach |
| 7,468,075 B2 | 12/2008 | Lang et al. |
| 7,497,029 B2 | 3/2009 | Plassky et al. |
| 7,520,880 B2 | 4/2009 | Claypool et al. |
| 7,547,307 B2 | 6/2009 | Carson et al. |
| 7,559,931 B2 | 7/2009 | Stone |
| 7,575,602 B2 | 8/2009 | Amirouche et al. |
| 7,578,821 B2 | 8/2009 | Fisher et al. |
| 7,591,854 B2 | 9/2009 | Wasielewski |
| 7,611,520 B2 | 11/2009 | Broers et al. |
| 7,611,522 B2 | 11/2009 | Gorek |
| 7,615,005 B2 | 11/2009 | Stefanchik et al. |
| 7,621,920 B2 | 11/2009 | Claypool et al. |
| 7,623,902 B2 | 11/2009 | Pacheco |
| 7,632,283 B2 | 12/2009 | Heldreth |
| 7,726,564 B2 | 6/2010 | Goldbach |
| 7,776,098 B2 | 8/2010 | Murphy |
| 7,831,292 B2 | 11/2010 | Quaid et al. |
| 7,834,847 B2 | 11/2010 | Boillot et al. |
| 7,837,691 B2 | 11/2010 | Cordes et al. |
| D629,900 S | 12/2010 | Fisher |
| 7,846,092 B2 | 12/2010 | Murphy |
| 7,857,821 B2 | 12/2010 | Couture et al. |
| 7,885,705 B2 | 2/2011 | Murphy |
| 7,918,887 B2 | 4/2011 | Roche |
| 7,927,336 B2 | 4/2011 | Rasmussen |
| 7,970,174 B2 | 6/2011 | Goldbach |
| 8,000,926 B2 | 8/2011 | Roche et al. |
| 8,057,479 B2 | 11/2011 | Stone |
| 8,057,482 B2 | 11/2011 | Stone |
| 8,075,254 B2 | 12/2011 | Morgan et al. |
| 8,098,544 B2 | 1/2012 | Roche et al. |
| 8,099,168 B2 | 1/2012 | Roche |
| 8,109,942 B2 | 2/2012 | Carson |
| 8,118,815 B2 | 2/2012 | Van Der Walt |
| 8,146,422 B2 | 4/2012 | Stein |
| 8,197,549 B2 | 6/2012 | Amirouche et al. |
| 8,211,041 B2 | 7/2012 | Fisher et al. |
| 8,241,296 B2 | 8/2012 | Wasielewski |
| 8,257,360 B2 | 9/2012 | Richard et al. |
| 8,265,790 B2 | 9/2012 | Amiot et al. |
| 8,267,938 B2 | 9/2012 | Murphy |
| 8,277,455 B2 | 10/2012 | Couture et al. |
| 8,282,646 B2 | 10/2012 | Schoenefeld et al. |
| 8,317,797 B2 | 11/2012 | Rasmussen |
| 8,337,428 B2 | 12/2012 | Stein et al. |
| 8,355,773 B2 | 1/2013 | Leitner et al. |
| 8,394,104 B2 | 3/2013 | Disilvestro |
| 8,421,308 B2 | 4/2013 | Adachi |
| 8,421,642 B1 | 4/2013 | Mcintosh et al. |
| 8,421,854 B2 | 4/2013 | Zerkin |
| 8,427,176 B2 | 4/2013 | Stein |
| 8,446,473 B2 | 5/2013 | Goldbach |
| 8,490,488 B2 | 7/2013 | Stein et al. |
| 8,491,589 B2 | 7/2013 | Fisher et al. |
| 8,506,571 B2 | 8/2013 | Chana et al. |
| 8,512,346 B2 | 8/2013 | Couture |
| 8,516,884 B2 | 8/2013 | Stein et al. |
| 8,516,907 B2 | 8/2013 | Stein et al. |
| 8,539,830 B2 | 9/2013 | Stein |
| 8,551,023 B2 | 10/2013 | Sherman et al. |
| 8,551,108 B2 | 10/2013 | Pelletier et al. |
| 8,556,830 B2 | 10/2013 | Sherman et al. |
| 8,556,972 B2 | 10/2013 | Gordon et al. |
| 8,588,892 B2 | 11/2013 | Hladio et al. |
| 8,661,893 B2 | 3/2014 | Stein et al. |
| 8,668,646 B2 | 3/2014 | Stein et al. |
| 8,679,186 B2 | 3/2014 | Stein et al. |
| 8,690,888 B2 | 4/2014 | Stein et al. |
| 8,696,756 B2 | 4/2014 | Stein et al. |
| 8,701,484 B2 | 4/2014 | Stein et al. |
| 8,707,782 B2 | 4/2014 | Stein et al. |
| 8,714,009 B2 | 5/2014 | Stein et al. |
| 8,715,290 B2 | 5/2014 | Fisher et al. |
| 8,718,820 B2 | 5/2014 | Amiot et al. |
| 8,720,270 B2 | 5/2014 | Stein et al. |
| 8,721,568 B2 | 5/2014 | Rock et al. |
| 8,734,454 B2 | 5/2014 | Disilvestro |
| 8,743,432 B2 | 6/2014 | Buswell et al. |
| 8,746,062 B2 | 6/2014 | Stein et al. |
| 8,758,355 B2 | 6/2014 | Fisher et al. |
| 8,764,758 B2 | 7/2014 | Echeverri |
| 8,777,877 B2 | 7/2014 | Stein et al. |
| 8,784,339 B2 | 7/2014 | Stein et al. |
| 8,814,810 B2 | 8/2014 | Roche et al. |
| 8,826,733 B2 | 9/2014 | Stein et al. |
| 8,828,013 B2 | 9/2014 | Fisher et al. |
| 8,864,686 B2 | 10/2014 | Roche et al. |
| 8,876,831 B2 | 11/2014 | Rasmussen |
| 8,888,786 B2 | 11/2014 | Stone |
| 8,906,027 B2 | 12/2014 | Roche |
| 8,906,107 B2 | 12/2014 | Bojarski et al. |
| 8,911,447 B2 | 12/2014 | Van Der Walt et al. |
| 8,911,448 B2 | 12/2014 | Stein |
| 8,926,530 B2 | 1/2015 | Stein et al. |
| 8,926,706 B2 | 1/2015 | Bojarski et al. |
| 8,939,030 B2 | 1/2015 | Stein et al. |
| 8,945,133 B2 | 2/2015 | Stein et al. |
| 8,974,467 B2 | 3/2015 | Stone |
| 8,974,468 B2 | 3/2015 | Borja |
| 8,974,539 B2 | 3/2015 | Bojarski et al. |
| 8,979,758 B2 | 3/2015 | Stein et al. |
| 8,998,910 B2 | 4/2015 | Borja et al. |
| 9,005,207 B2 | 4/2015 | Dodds et al. |
| 9,011,448 B2 | 4/2015 | Roche et al. |
| 9,095,275 B2 | 8/2015 | Clark |
| 9,095,352 B2 | 8/2015 | Fisher et al. |
| 9,141,254 B2 | 9/2015 | Boillot et al. |
| 9,161,717 B2 | 10/2015 | Stein et al. |
| 9,168,032 B2 | 10/2015 | Hutchison et al. |
| 9,189,083 B2 | 11/2015 | Roche et al. |
| 9,192,392 B2 | 11/2015 | Van Der Walt et al. |
| 9,199,733 B2 | 12/2015 | Keennon et al. |
| 9,226,694 B2 | 1/2016 | Stein et al. |
| 9,232,951 B2 | 1/2016 | Johannaber |
| 9,237,885 B2 | 1/2016 | Stein et al. |
| 9,259,172 B2 | 2/2016 | Stein et al. |
| 9,259,179 B2 | 2/2016 | Stein |
| 9,262,802 B2 | 2/2016 | Aghazadeh |
| 9,265,447 B2 | 2/2016 | Stein et al. |
| 9,271,675 B2 | 3/2016 | Stein et al. |
| 9,271,756 B2 | 3/2016 | Van Der Walt et al. |
| 9,289,163 B2 | 3/2016 | Stein et al. |
| 9,332,943 B2 | 5/2016 | Stein et al. |
| 9,339,212 B2 | 5/2016 | Stein et al. |
| 9,339,226 B2 | 5/2016 | Van Der Walt et al. |
| 9,345,449 B2 | 5/2016 | Stein et al. |
| 9,345,492 B2 | 5/2016 | Stein et al. |
| 9,351,782 B2 | 5/2016 | Stein et al. |
| 9,358,136 B2 | 6/2016 | Stein et al. |
| 9,375,178 B2 | 6/2016 | Aghazadeh |
| 2002/0077540 A1 | 6/2002 | Kienzie, III |
| 2002/0103610 A1 | 8/2002 | Bachmann et al. |
| 2002/0107522 A1 | 8/2002 | Picard et al. |
| 2002/0133175 A1 | 9/2002 | Carson |
| 2002/0198451 A1 | 12/2002 | Carson |

(56) References Cited

U.S. PATENT DOCUMENTS

| | | |
|---|---|---|
| 2003/0019294 A1 | 1/2003 | Richter |
| 2003/0069591 A1 | 4/2003 | Carson et al. |
| 2003/0093080 A1 | 5/2003 | Brown et al. |
| 2003/0105470 A1 | 6/2003 | White |
| 2003/0120282 A1 | 6/2003 | Scouten et al. |
| 2003/0153978 A1 | 8/2003 | Whiteside |
| 2003/0163142 A1 | 8/2003 | Paltieli et al. |
| 2003/0184297 A1 | 10/2003 | Jakab |
| 2003/0199882 A1 | 10/2003 | Gorek |
| 2003/0204965 A1 | 11/2003 | Hennessey |
| 2003/0229356 A1 | 12/2003 | Dye |
| 2004/0006393 A1 | 1/2004 | Burkinshaw |
| 2004/0019382 A1 | 1/2004 | Amirouche et al. |
| 2004/0034313 A1 | 2/2004 | Leitner |
| 2004/0039396 A1 | 2/2004 | Couture et al. |
| 2004/0068260 A1 | 4/2004 | Cossette et al. |
| 2004/0087962 A1 | 5/2004 | Gorek |
| 2004/0097952 A1 | 5/2004 | Sarin et al. |
| 2004/0102792 A1 | 5/2004 | Sarin et al. |
| 2004/0106916 A1 | 6/2004 | Quaid et al. |
| 2004/0147926 A1 | 7/2004 | Iversen |
| 2004/0149036 A1 | 8/2004 | Foxlin et al. |
| 2004/0152970 A1 | 8/2004 | Hunter et al. |
| 2004/0153066 A1 | 8/2004 | Coon et al. |
| 2004/0153079 A1 | 8/2004 | Tsougarakis et al. |
| 2004/0181144 A1 | 9/2004 | Cinquin et al. |
| 2004/0201857 A1 | 10/2004 | Foxlin |
| 2004/0243148 A1 | 12/2004 | Wasielewski |
| 2005/0021037 A1 | 1/2005 | McCombs et al. |
| 2005/0021044 A1 | 1/2005 | Stone et al. |
| 2005/0038442 A1 | 2/2005 | Freeman |
| 2005/0107799 A1 | 5/2005 | Graf et al. |
| 2005/0113846 A1 | 5/2005 | Carson |
| 2005/0149040 A1 | 7/2005 | Haines et al. |
| 2005/0197814 A1 | 9/2005 | Aram et al. |
| 2005/0209605 A1 | 9/2005 | Grimm et al. |
| 2005/0222574 A1 | 10/2005 | Giordano et al. |
| 2005/0234332 A1* | 10/2005 | Murphy ............... A61B 5/4528 600/426 |
| 2005/0251026 A1 | 11/2005 | Stone |
| 2005/0251148 A1 | 11/2005 | Friedrich |
| 2006/0015018 A1 | 1/2006 | Jutras et al. |
| 2006/0015120 A1 | 1/2006 | Richard et al. |
| 2006/0020177 A1 | 1/2006 | Seo et al. |
| 2006/0064105 A1 | 3/2006 | Raistrick et al. |
| 2006/0089657 A1 | 4/2006 | Broers et al. |
| 2006/0094958 A1 | 5/2006 | Marquart et al. |
| 2006/0122491 A1 | 6/2006 | Murray et al. |
| 2006/0142656 A1 | 6/2006 | Malackowski et al. |
| 2006/0142657 A1 | 6/2006 | Quaid et al. |
| 2006/0161051 A1* | 7/2006 | Terrill-Grisoni ....... A61B 90/36 600/300 |
| 2006/0217733 A1 | 9/2006 | Plassky et al. |
| 2006/0217734 A1 | 9/2006 | Sanford et al. |
| 2006/0241639 A1 | 10/2006 | Kuczynski et al. |
| 2006/0270949 A1 | 11/2006 | Mathie et al. |
| 2006/0282023 A1 | 12/2006 | Leitner |
| 2007/0032748 A1 | 2/2007 | McNeil et al. |
| 2007/0043287 A1 | 2/2007 | Degraaf |
| 2007/0066917 A1 | 3/2007 | Hodorek et al. |
| 2007/0118139 A1 | 5/2007 | Cuellar et al. |
| 2007/0162142 A1 | 7/2007 | Stone |
| 2007/0179626 A1 | 8/2007 | de la Barrera et al. |
| 2007/0219561 A1 | 9/2007 | Lavallee et al. |
| 2007/0226986 A1 | 10/2007 | Park et al. |
| 2007/0249967 A1 | 10/2007 | Buly et al. |
| 2007/0270973 A1 | 11/2007 | Johnson et al. |
| 2007/0287911 A1 | 12/2007 | Haid et al. |
| 2008/0039868 A1 | 2/2008 | Tuemmler et al. |
| 2008/0058945 A1 | 3/2008 | Hajaj et al. |
| 2008/0071195 A1 | 3/2008 | Cuellar et al. |
| 2008/0103509 A1 | 5/2008 | Goldbach |
| 2008/0162074 A1 | 7/2008 | Schneider |
| 2008/0183179 A1 | 7/2008 | Siebel et al. |
| 2008/0195109 A1 | 8/2008 | Hunter et al. |
| 2008/0202200 A1 | 8/2008 | West |
| 2008/0211768 A1 | 9/2008 | Breen et al. |
| 2008/0243127 A1 | 10/2008 | Lang et al. |
| 2008/0249394 A1 | 10/2008 | Giori et al. |
| 2008/0262812 A1 | 10/2008 | Arata et al. |
| 2008/0275451 A1 | 11/2008 | McAllister et al. |
| 2008/0281328 A1 | 11/2008 | Lang et al. |
| 2008/0285805 A1 | 11/2008 | Luinge et al. |
| 2009/0000626 A1 | 1/2009 | Quaid et al. |
| 2009/0000627 A1 | 1/2009 | Quaid et al. |
| 2009/0012532 A1 | 1/2009 | Quaid et al. |
| 2009/0018544 A1 | 1/2009 | Heavener |
| 2009/0040224 A1 | 2/2009 | Igarashi et al. |
| 2009/0088753 A1 | 4/2009 | Aram et al. |
| 2009/0138019 A1 | 5/2009 | Wasielewski |
| 2009/0171370 A1 | 7/2009 | Yoon et al. |
| 2009/0209884 A1 | 8/2009 | Van Vorhis et al. |
| 2009/0216247 A1 | 8/2009 | Collette |
| 2009/0234360 A1 | 9/2009 | Alexander |
| 2009/0247863 A1 | 10/2009 | Proulx et al. |
| 2009/0248044 A1 | 10/2009 | Amiot et al. |
| 2009/0264737 A1 | 10/2009 | Haechler et al. |
| 2009/0270864 A1 | 10/2009 | Poncet |
| 2009/0270865 A1 | 10/2009 | Poncet et al. |
| 2009/0270868 A1 | 10/2009 | Park et al. |
| 2009/0270869 A1 | 10/2009 | Colquhoun et al. |
| 2009/0270874 A1 | 10/2009 | Santarella et al. |
| 2009/0270875 A1 | 10/2009 | Poncet |
| 2009/0270928 A1 | 10/2009 | Stone et al. |
| 2009/0276054 A1 | 11/2009 | Clifford et al. |
| 2009/0281545 A1 | 11/2009 | Stubbs |
| 2009/0292227 A1 | 11/2009 | Scholten et al. |
| 2009/0299416 A1 | 12/2009 | Haenni et al. |
| 2009/0299483 A1 | 12/2009 | Amirouche et al. |
| 2009/0306679 A1 | 12/2009 | Murphy |
| 2009/0312973 A1 | 12/2009 | Hatlestad et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0324078 A1 | 12/2009 | Wu et al. |
| 2010/0010506 A1 | 1/2010 | Murphy |
| 2010/0016705 A1 | 1/2010 | Stone |
| 2010/0023018 A1 | 1/2010 | Theofilos |
| 2010/0063508 A1* | 3/2010 | Borja .................. A61B 17/154 606/88 |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0100011 A1 | 4/2010 | Roche |
| 2010/0100154 A1 | 4/2010 | Roche |
| 2010/0113980 A1 | 5/2010 | Herr et al. |
| 2010/0121334 A1 | 5/2010 | Couture et al. |
| 2010/0137871 A1 | 6/2010 | Borja |
| 2010/0153081 A1 | 6/2010 | Bellettre et al. |
| 2010/0179605 A1 | 7/2010 | Branch et al. |
| 2010/0182914 A1 | 7/2010 | DelRegno et al. |
| 2010/0192662 A1 | 8/2010 | Yanni |
| 2010/0198067 A1 | 8/2010 | Mahfouz et al. |
| 2010/0198275 A1 | 8/2010 | Chana et al. |
| 2010/0204551 A1 | 8/2010 | Roche |
| 2010/0204575 A1 | 8/2010 | Roche et al. |
| 2010/0204955 A1 | 8/2010 | Roche et al. |
| 2010/0211077 A1 | 8/2010 | Couture et al. |
| 2010/0239996 A1 | 9/2010 | Ertl |
| 2010/0249533 A1 | 9/2010 | Pierce et al. |
| 2010/0249534 A1 | 9/2010 | Pierce et al. |
| 2010/0249535 A1 | 9/2010 | Pierce et al. |
| 2010/0249659 A1 | 9/2010 | Sherman et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250276 A1 | 9/2010 | Pierce et al. |
| 2010/0250284 A1 | 9/2010 | Roche et al. |
| 2010/0250571 A1 | 9/2010 | Pierce et al. |
| 2010/0256504 A1 | 10/2010 | Moreau-Gaudry et al. |
| 2010/0261998 A1 | 10/2010 | Stiehl |

(56) References Cited

U.S. PATENT DOCUMENTS

| | | |
|---|---|---|
| 2010/0268067 A1 | 10/2010 | Razzaque et al. |
| 2010/0298661 A1 | 11/2010 | McCombie et al. |
| 2010/0324457 A1 | 12/2010 | Bean et al. |
| 2010/0326187 A1 | 12/2010 | Stein |
| 2010/0326194 A1 | 12/2010 | Stein et al. |
| 2010/0326210 A1 | 12/2010 | Stein et al. |
| 2010/0326211 A1 | 12/2010 | Stein |
| 2010/0327848 A1 | 12/2010 | Stein |
| 2010/0327880 A1 | 12/2010 | Stein |
| 2010/0328077 A1 | 12/2010 | Stein |
| 2010/0328098 A1 | 12/2010 | Stein et al. |
| 2010/0331633 A1 | 12/2010 | Stein |
| 2010/0331663 A1 | 12/2010 | Stein |
| 2010/0331679 A1 | 12/2010 | Stein |
| 2010/0331680 A1 | 12/2010 | Stein |
| 2010/0331681 A1 | 12/2010 | Stein et al. |
| 2010/0331682 A1 | 12/2010 | Stein et al. |
| 2010/0331683 A1 | 12/2010 | Stein et al. |
| 2010/0331685 A1 | 12/2010 | Stein et al. |
| 2010/0331687 A1 | 12/2010 | Stein et al. |
| 2010/0331704 A1 | 12/2010 | Stein et al. |
| 2010/0331718 A1 | 12/2010 | Stein |
| 2010/0331733 A1 | 12/2010 | Stein |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2010/0331894 A1 | 12/2010 | Stein |
| 2010/0332152 A1 | 12/2010 | Stein |
| 2011/0028865 A1 | 2/2011 | Luinge et al. |
| 2011/0032184 A1 | 2/2011 | Roche et al. |
| 2011/0093081 A1 | 4/2011 | Chana et al. |
| 2011/0160572 A1 | 6/2011 | Mcintosh et al. |
| 2011/0160616 A1 | 6/2011 | Stein et al. |
| 2011/0160738 A1 | 6/2011 | Mcintosh et al. |
| 2011/0208093 A1 | 8/2011 | Gross et al. |
| 2011/0213275 A1 | 9/2011 | Boos et al. |
| 2011/0218458 A1 | 9/2011 | Valin et al. |
| 2011/0218546 A1 | 9/2011 | De La Fuente Klein et al. |
| 2011/0275957 A1 | 11/2011 | Bhandari |
| 2012/0029389 A1 | 2/2012 | Amiot et al. |
| 2012/0053488 A1 | 3/2012 | Boutin et al. |
| 2012/0053594 A1 | 3/2012 | Pelletier et al. |
| 2012/0093377 A1 | 4/2012 | Tsougarakis et al. |
| 2012/0157887 A1 | 6/2012 | Fanson et al. |
| 2012/0172712 A1 | 7/2012 | Bar-Tal |
| 2012/0172762 A1 | 7/2012 | Boyer et al. |
| 2012/0203140 A1 | 8/2012 | Malchau et al. |
| 2012/0209117 A1 | 8/2012 | Mozes et al. |
| 2012/0232429 A1 | 9/2012 | Fischer et al. |
| 2012/0290088 A1 | 11/2012 | Amirouche et al. |
| 2012/0316567 A1 | 12/2012 | Gross et al. |
| 2012/0330367 A1 | 12/2012 | Roche et al. |
| 2013/0023794 A1 | 1/2013 | Stein et al. |
| 2013/0023795 A1 | 1/2013 | Stein et al. |
| 2013/0079668 A1 | 3/2013 | Stein et al. |
| 2013/0079669 A1 | 3/2013 | Stein et al. |
| 2013/0079670 A1 | 3/2013 | Stein et al. |
| 2013/0079671 A1 | 3/2013 | Stein et al. |
| 2013/0079675 A1 | 3/2013 | Stein et al. |
| 2013/0079678 A1 | 3/2013 | Stein et al. |
| 2013/0079679 A1 | 3/2013 | Roche et al. |
| 2013/0079680 A1 | 3/2013 | Stein et al. |
| 2013/0079790 A1 | 3/2013 | Stein et al. |
| 2013/0079791 A1 | 3/2013 | Stein et al. |
| 2013/0079793 A1 | 3/2013 | Stein et al. |
| 2013/0079884 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0110250 A1 | 5/2013 | Li |
| 2013/0190887 A1 | 7/2013 | Fanson et al. |
| 2013/0203031 A1 | 8/2013 | Mckinnon et al. |
| 2013/0226034 A1 | 8/2013 | Stein et al. |
| 2013/0226035 A1 | 8/2013 | Stein et al. |
| 2013/0226036 A1 | 8/2013 | Stein et al. |
| 2013/0226190 A1 | 8/2013 | Mckinnon et al. |
| 2013/0261758 A1 | 10/2013 | Claypool et al. |
| 2013/0274633 A1 | 10/2013 | Hladio et al. |
| 2013/0296860 A1 | 11/2013 | Chana et al. |
| 2013/0331850 A1 | 12/2013 | Bojarski et al. |
| 2014/0005673 A1 | 1/2014 | Pelletier et al. |
| 2014/0018707 A1 | 1/2014 | Sherman et al. |
| 2014/0031672 A1 | 1/2014 | McCaulley et al. |
| 2014/0052149 A1 | 2/2014 | Van Der Walt et al. |
| 2014/0094715 A1 | 4/2014 | Stein et al. |
| 2014/0107796 A1 | 4/2014 | Stein et al. |
| 2014/0114179 A1 | 4/2014 | Muller et al. |
| 2014/0134586 A1 | 5/2014 | Stein et al. |
| 2014/0135624 A1 | 5/2014 | Stein et al. |
| 2014/0135655 A1 | 5/2014 | Stein et al. |
| 2014/0135658 A1 | 5/2014 | Hladio et al. |
| 2014/0135744 A1 | 5/2014 | Stein et al. |
| 2014/0135773 A1 | 5/2014 | Stein et al. |
| 2014/0136143 A1 | 5/2014 | Stein et al. |
| 2014/0148676 A1 | 5/2014 | Stein et al. |
| 2014/0171754 A1 | 6/2014 | Stein et al. |
| 2014/0182062 A1 | 7/2014 | Aghazadeh |
| 2014/0222007 A1 | 8/2014 | Rock et al. |
| 2014/0228851 A1 | 8/2014 | Guloy, Jr. et al. |
| 2014/0276000 A1 | 9/2014 | Mullaney et al. |
| 2014/0276240 A1 | 9/2014 | Stein et al. |
| 2014/0276241 A1 | 9/2014 | Stein et al. |
| 2014/0276860 A1 | 9/2014 | Stein et al. |
| 2014/0276861 A1 | 9/2014 | Stein et al. |
| 2014/0276863 A1 | 9/2014 | Stein et al. |
| 2014/0276864 A1 | 9/2014 | Aghazadeh |
| 2014/0276885 A1 | 9/2014 | Stein et al. |
| 2014/0276886 A1 | 9/2014 | Stein et al. |
| 2014/0277526 A1 | 9/2014 | Stein et al. |
| 2014/0277542 A1 | 9/2014 | Stein et al. |
| 2014/0288563 A1 | 9/2014 | Claypool et al. |
| 2014/0296860 A1 | 10/2014 | Stein et al. |
| 2014/0330105 A1 | 11/2014 | Roche |
| 2014/0330281 A1 | 11/2014 | Aghazadeh |
| 2014/0364858 A1 | 12/2014 | Li et al. |
| 2015/0018718 A1 | 1/2015 | Aghazadeh |
| 2015/0080901 A1 | 3/2015 | Stein |
| 2015/0100058 A1 | 4/2015 | Van Der Walt et al. |
| 2015/0100059 A1 | 4/2015 | Chana et al. |
| 2015/0106024 A1 | 4/2015 | Lightcap et al. |
| 2015/0150569 A1 | 6/2015 | Van Der Walt et al. |
| 2015/0157335 A1 | 6/2015 | Rasmussen |
| 2015/0238204 A1 | 8/2015 | Stone |
| 2015/0265363 A1 | 9/2015 | White et al. |
| 2015/0272478 A1 | 10/2015 | Borja |
| 2015/0272597 A1 | 10/2015 | Johannaber |
| 2015/0313725 A1 | 11/2015 | Fisher et al. |
| 2015/0335448 A1 | 11/2015 | Lorio et al. |
| 2015/0342516 A1 | 12/2015 | Nguyen et al. |
| 2016/0030156 A1 | 2/2016 | Cole |
| 2016/0074053 A1 | 3/2016 | Hutchison et al. |
| 2016/0081762 A1 | 3/2016 | Stein et al. |
| 2016/0089079 A1 | 3/2016 | Stein |
| 2016/0213383 A1 | 7/2016 | Van Der Walt et al. |

FOREIGN PATENT DOCUMENTS

| | | |
|---|---|---|
| CA | 2 537 711 | 8/2007 |
| DE | 4 225 112 | 12/1993 |
| DE | 29704393 | 8/1997 |
| DE | 198 30 359 | 1/2000 |
| EP | 0 557 591 | 9/1993 |
| EP | 0 675 698 | 10/1995 |
| EP | 1 304 093 | 10/2005 |
| EP | 1 814 471 | 3/2010 |
| EP | 1 817 547 | 4/2012 |
| EP | 2 567 665 | 3/2013 |
| EP | 2 588 030 | 5/2013 |
| EP | 2 822 481 | 1/2015 |
| GB | 2 197 790 | 6/1988 |
| JP | 07-184929 | 7/1995 |
| JP | H08-240611 | 9/1996 |

(56) References Cited

FOREIGN PATENT DOCUMENTS

| | | |
|---|---|---|
| JP | 2006-314775 | 11/2006 |
| JP | 2007-503289 | 2/2007 |
| JP | 2007-534351 | 11/2007 |
| WO | WO 94/020040 | 9/1994 |
| WO | WO 94/027516 | 12/1994 |
| WO | WO 99/60939 | 12/1999 |
| WO | WO 01/30247 | 5/2001 |
| WO | WO 02/00131 | 1/2002 |
| WO | WO 02/17798 | 3/2002 |
| WO | WO 2004/080323 | 9/2004 |
| WO | WO 2004/112610 | 12/2004 |
| WO | WO 2005/006993 | 1/2005 |
| WO | WO 2006/078236 | 7/2006 |
| WO | WO 2006/119387 | 11/2006 |
| WO | WO 2006/136836 | 12/2006 |
| WO | WO 2007/136784 | 11/2007 |
| WO | WO 2008/073999 | 6/2008 |
| WO | WO 2008/129414 | 10/2008 |
| WO | WO 2009/117833 | 10/2009 |
| WO | WO 2010/011978 | 1/2010 |
| WO | WO 2010/030809 | 3/2010 |
| WO | WO 2011/044273 | 4/2011 |
| WO | WO 2012/006172 | 1/2012 |
| WO | WO 2012/027815 | 3/2012 |
| WO | WO 2012/027816 | 3/2012 |
| WO | WO 2012/082164 | 6/2012 |
| WO | WO 2012/113054 | 8/2012 |
| WO | WO 2013/012561 | 1/2013 |
| WO | WO 2013/044157 | 3/2013 |
| WO | WO 2013/044165 | 5/2013 |
| WO | WO 2013/044174 | 7/2013 |
| WO | WO 2013/169674 | 11/2013 |
| WO | WO 2013/173700 | 11/2013 |
| WO | WO 2013/188960 | 12/2013 |
| WO | WO 2014/028227 | 2/2014 |
| WO | WO 2015/038979 | 3/2015 |

OTHER PUBLICATIONS 510 (k) Summary for Total Knee Surgetics Navigation System, in 5 pages.
510 (k) Summary of Safety and Effectiveness for BrainLAB knee, in 5 pages.
Anderson MD., Kevin, et al., "Computer Assisted Navigation in Total Knee Arthroplasty", The Journal of Arthroplasty, 2005, vol. 20, No. 7, Suppl. 3, in 7 pages.
Ang, et al., An Active Hand-Held Instrument for Enhanced Microsurgical Accuracy, Medical Image Computing and Computer-Assisted Intervention, 2000, vol. 1935, pp. 878-887.
Arnold-Moore, et. al., Architecture of a Content Management Server for XML Document Applications, RMIT Multimedia Database Systems, Royal Melbourne Institute of Technology, Victoria Australia, in 12 pages.
ArthroCAD, Enhancing orthopedic outcomes through optimal alignment, 2012, Pages in 2 pages.
Bae et al., "Computer Assisted Navigation in Knee Arthroplasty", Clinics in Orthopedic Surgery, 2011, vol. 3, pp. 259-267.
Bargren, MD., et al,, Alignment in Total Knee Arthroplasty, Correlated Biomechanical and Clinical Observations, Clinical Orthopaedics and Related Research, Mar. 1, 1983, Issue 173, pp. 178-183, Philadelphia.
Bathis, H. et al., "Alignment in total knee arthroplasty", The Journal of Bone & Joint Surgery (Br), 2004, 86-B, pp. 682-687, British Editorial.
Bhandari, Design and Prototype of a Computer Assisted Surgical Navigation System for Total Knee Replacement Surgery, May 12, 2009, Pages in 294 pages.
Biomet Orthopedics, Inc, Vision Acetabular Surgical Techniques, website brochure, pp. 16 pages.
Biomet Orthopedics, Inc., Universal Ringlock® Acetabular Series, Vol. website brochure, pp. 13 pages.
Brennan, et al., Quantification of Inertial Sensor-Based 3D Joint Angle Measurement Accuracy Using and Instrumented Gimbal, Gait & Posture, May 23, 2011, vol. 34, pp. 320-323.
Chauhan, et al., Computer-Assisted Knee Arthroplasty Versus a Conventional Jig-Based Technique, The Journal of Bone & Joint Surge 2004, vol. 86-B, pp. 372-377.
Cutti, et al., Motion Analysis of the Upper-Limb Based on Inertial Sensors: Part 1—Protocol Description, Journal of Biomechanics, Jan. 1, 2007, vol. 40, pp. S250.
Decking, MD., et al., Leg Axis After Computer-Navigated Total Knee Arthroplasty, The Journal of Arthroplasty, 2005, vol. 20, Issue 3, pp. 282-288.
Depuy, Johnson & Johnson, Co.,, Summit Cemented Hip System, website brochure, pp. 21 pages.
Digioia III, MD., et al., "Comparison of a Mechanical Acetabular Alignment Guide with Computer Placement of the Socket", The Journal of Arthroplasty, Apr. 2002, vol. 17, No. 3, in 6 pages.
Eric Foxlin, Chapter 7. Motion Tracking Requirements and Technologies, Handbook of Virtual Environment Technology, 2002, vol. Kay Stanney, Ed., Issue Lawrence Erlbaum Ass.
Favre, et al., 3D Evaluation of the Knee Joint Using Ambulatory System: Application to ACL-Deficient Knees, Journal of Biomechanics, Jan. 1, 2007, vol. 40, pp. S251.
Favre, et al., A New Ambulatory System for Comparative Evaluation of the Three-Dimensional Knee Kinematics, Applied to Anterior Cruciate Ligament Injuries, Knee Surgery, Sports Traumatology, Arthroscopy, Jan. 19, 2006, vol. 14, pp. 592-604.
Favre, et al., Ambulatory Measurement of 3D Knee Joint Angle, Journal of Biomechanics, Jan. 28, 2008, vol. 41, Issue 1029-1035.
Fixed Reference Surgical Technique, SIGMA High Performance Instruments, DePuy Orthopaedics, Inc., 2008, Warsaw, IN, in 52pages.
Ganapathi et al., "Limb Length and Femoral Offset Reconstruction During THA Using CT-Free Computer Navigation", The Journal of Bone and Joint Surgery, 2009, vol. 91-B, Supplement III, p. 399.
Goniometer, AllHeart.com, 2004, website: http://allheart.com/allheart, (1 page).
Haaker et al., "Computer-Assisted Navigation Increases Precision of Component Placement in Total Knee Arthroplasty", Clinical Orthopaedics and Related Research, Apr. 2005, vol. 433, pp. 152-159.
Hofstetter, Ph.D., et al., "Computer-Assisted Fluoroscopy-Based Reduction of Femoral Fractures and Antetorsion Correction", Computer Aided Surgery, 2000, vol. 5, pp. 311-325, Wiley-Liss, Inc.
Hsieh, Pang-Hsin, et al., "Image-guided periacetabular osteotomy: computer-assisted navigation compared with the conventional technique: A randomized study of 36 patients followed for 2 years", Acta Orthopaedica, Aug. 1, 2006, 77:4, pp. 591-597.
International Preliminary Report for Application No. PCT/US2004/018244, dated Dec. 13, 2005, in 11 pages.
International Search Report and Written Opinion issued in PCT Application No. PCT/US2013/039770, dated Sep. 25, 2013.
International Preliminary Report on Patentability issued in PCT Application No. PCT/US2013/039770, dated Nov. 11, 2014.
International Search Report and Written Opinion issued in PCT Application No. PCT/US2013/041556, dated Sep. 13, 2013.
International Preliminary Report on Patentability issued in PCT Application No. PCT/US2013/041556, dated Nov. 18, 2014.
International Search Report and Written Opinion issued in PCT Application No. PCT/US2013/053182, dated Nov. 11, 2013.
International Search Report for Application No. PCT/US2004/018244, dated Feb. 15, 2005, in 4 pages.
International Search Report for International Application No. PCT/US2009/051769 dated Nov. 19, 2009, in 11 pages.
International Search Report for International Application No. PCT/US2009/051769 dated Nov. 19, 2009, in 3 pages.
International Search Report for International Application No. PCT/US2011/022162, dated Jun. 16, 2011, in 4 pages.
International Search Report for International Application No. PCT/US2009/056553, dated Nov. 4, 2009, in 12 pages.
International Preliminary Report on Patentability issued in PCT Application No. PCT/US2013/053182, dated Feb. 17, 2015, in 10 pages.

(56) References Cited

OTHER PUBLICATIONS

Jenny, et al., Computer-Assisted Implantation of Total Knee Prosthesis: A Case-Control Comparative Study with Classical Instrumentation, Computer Aided Surgery, 2001, vol. 6, pp. 217-220.
Konyves et al., "The importance of leg length discrepancy after total hip arthroplasty", The Journal of Bone & Joint Surgery (Br), Feb. 2005, vol. 87-B, No. 2, pp. 155-157.
Leenders, MD., et al., "Reduction in Variability of Acetabular Cup Abduction Using Computer Assisted Surgery: A Prospective and Randomized Study", Computer Aided Surgery, 2002, vol. 7, pp. 99-106.
Leung, et al., Intraobserver Errors in Obtaining Visually Selected Anatomic Landmarks During Registration Process in Nonimage-based Navigation-assisted Total Knee Arthroplasty, The Journal of Arthroplasty, 2005, vol. 20, Issue 5, pp. 591-601.
Liebergall, Meir, et al., "Computerized Navigation for the Internal Fixation of Femoral Neck Fractures", The Journal of Bone & Joint Surgery Am, 2006, vol. 88, pp. 1748-1754.
Longo, et al., MIKA Surgical Technique, DJO Surgical, 2008, Austin Texas in 14 pages.
Luinge, Inertial Sensing of Human Movement, Twente University Press, Feb. 15, 1973, Pages in 88 pages.
Mackenzie, et al., A Two-Ball Mouse Affords Three Degrees of Freedom, Extended Abstracts of the CHI '97 Conference on Human Factors in Compounding Systems (as printed from the internet on Jun. 13, 2012 URL: http://www.yorku.ca/mack/CHI97a.htm), 1997, pp. 303-304.
Medical Research Ltd, Clinical Goniometer, http://www.mie-uk.com/Gonio, 1997, pp. 1 page.
Minimally Invasive TKA GENESIS II Anterior Cut First, Surgical Technique, Smith & Nephew, Nov. 2003, Memphis TN, in 16 pages.
Noble et al., "Computer Simulation: How Can it Help the Surgeon Optimize Implant Position?", Clinical Orthopaedics and Related Research, Dec. 2003, vol. 417, pp. 242-252.
Parratte, Sebastien, et al., "Validation and Usefulness of a Computer-Assisted Cup-Positioning System in Total Hip Arthroplasty. A Prospective, Randomized, Controlled Study", The Journal of Bone & Joint Surgery Am, 2007, vol. 89, pp. 494-499.
Ritter, M.D., et al., Postoperative Alignment of Total Knee Replacement, Its Effect on Survival, Clinical Orthopaedics and Related Research, Feb. 1, 1994, Issue 299, pp. 153-156, Philadelphia.
Rocon, et al., Application of Inertial Sensors and Rehabilitation Robotics, Rehabilitation Robotics 2007, Jun. 1, 2007, pp. 145-150.
Sacks-Davis et. Al., Atlas: A nested Relational Database System for Text Applications, IEEE Transations on Knowledge and Data Engineering, v.7, n.3, Jun. 1995, pp. 454-470.
Schep, et al., "Computer assisted orthopaedic and trauma surgery State of the art and future perspectives", Injury Int. J. Care Injured 34, (website: www.elsevier.com/locate/injury), 2003 pp. 299-306.
Scott, M.S., et al., P.F.C. Sigma Knee System, Primary Surgical Technique Part 1 of 2, DePuy International Ltd., 2003, England, (up to p. 44), in 48 pages.
Scott, M.S., et al., P.F.C. Sigma Knee System, Primary Surgical Technique Part 2 of 2, DePuy International Ltd., 2003, England, Part A (up to p. 74), in 31 pages.
Scott, M.S., et al., P.F.C. Sigma Knee System, Primary Surgical Technique Part 2 of 2, DePuy International Ltd., 2003, England, Part B (up to p. 104), in 31 pages.
Sikorski et al., "Computer-Assisted Orthopaedic Surgery: Do We Need CAOS?", The Journal of Bone & Joint Surgery (Br), Apr. 2003, vol. 85-B, No. 3, pp. 319-323.
Slomczykowski, et al., "Novel Computer-Assisted Fluoroscopy System for Intraoperative Guidance: Feasibility Study for Distal Locking of Femoral Nails", Journal of Orthopaedic Trauma, 2001, vol. 15, No. 2, pp. 122-131, Lippincott Williams & Wilkins, Inc., Philadelphia.
Stulberg, et al., Computer-Assisted Total Knee Replacement Arthroplasty, Operative Techniques in Orthopaedics, Jan. 2000, vol. 10, Issue 1, pp. 25-39.
The Academy of Orthopaedic Surgeons, Academy News, http://www.aaos.org/wordhtml/2001news/b6-01.htm, Mar. 1, 2001, pp. 1 page.
Tilt Sensors: High Accuracy, Digital Series, Crossbow Technology, Inc., pp. 32-35.
Upadhyay et al., "Medical Malpractice in Hip and Knee Arthroplasty", The Journal of Arthroplasty, 2007, vol. 22, No. 6, Suppl. 2, pp. 2-7.
Visser, et al., 3D Analysis of Upper Body Movements in Bilateral Amputee Gait Using Inertial Sensors, Journal of Biomechanics, Jan. 1, 2007, vol. 40, Issue S509.
Written Opinion for International Application No. PCT/US2009/051769, dated Nov. 19, 2009, in 7 pages.
Written Opinion for International Application No. PCT/US2011/022162, dated Jun. 16, 2011, in 9 pages.
Written Opinion of the ISR for Application No. PCT/US2004/018244, received Mar. 14, 2005, in 10 pages.
Wylde et al., "Prevalence and functional impact of patient-perceived leg length discrepancy after hip replacement", International Orthopaedics, 2009, vol. 33, pp. 905-909.
Wylde et al., "Patient-perceived leg length discrepancy after total hip replacement: prevalence and impact on functional outcome", International Orthopaedics, 2008, vol. 24, No. 2, pp. 210-216.
Zhou, et al., Use of Multiple Wearable Inertial Sensors in Upper Limb Motion Tracking, Medical Engineering & Physics, Jan. 1, 2008, vol. 30, pp. 123-133.
Zimmer NexGen Flexion Balancing Instruments, Surgical Technique, 2007, www.zimmer.com, in 44 pages.
Zorman, David, et al., "Computer-assisted total knee arthroplasty: comparative results in a preliminary series of 72 cases", ActaOrthop. Belg., 2005, 71, pp. 696-702.
Brainlab, "Position Determination and Calibration in optical tracking systems", Florenus the technology merchants, in 2 pages.
Brainlab, "Tracking and imaging in Navigation", Florenus, in 2 pages.
De Momi, et al., "In-vitro experimental assessment of a new robust algorithm for hip joint centre estimation", Journal of Biomechanics, Feb. 26, 2009, vol. 42, pp. 989-995.
International Search Report and Written Opinion issued in International Application No. PCT/US2016/018508, dated Jun. 22, 2016, in 19 pages.
Perseus Intelligent Cutting Guide, Orthokey, Product Guide, in 8 pages.
Perseus Intelligent Cutting Guide, Smart Instruments for Knee Arthroplasty, Orthokey, in 2 pages.

\* cited by examiner

DEVICES AND METHODS FOR KNEE ARTHROPLASTY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present application includes inventions that provide devices and/or methods to assist in the distal femur resection and/or the proximal tibial resection during knee arthroplasty.

Description of the Related Art

The knee joint often requires replacement in the form of prosthetic components due to strain, stress, wear, deformation, misalignment, and/or other conditions in the joint. Prosthetic knee joint components are designed to replace a distal portion or portions of a femur and/or a proximal portion or portions of a tibia. Prior to replacing the knee joint with prosthetic components, surgical cuts commonly called resections are generally made with a cutting tool or tools along a portion or portions of both the proximal tibia and distal femur. These cuts are made to prepare the tibia and femur for the prosthetic components. After these cuts are made, the prosthetic components can be attached and/or secured to the tibia and femur.

Resecting a portion or portions of the distal femur can provide a location for placement and/or attachment of a femoral knee joint prosthetic ("distal femoral resection"). The orientation of a cutting block, and/or cutting plane or planes, can be pre-operatively determined in order to provide a desired fit and/or orientation for the femoral knee joint prosthetic. Properly orientating the cutting plane or planes along the distal femur can facilitate alignment of the femoral knee joint prosthetic with the tibial knee joint prosthetic. This alignment can create a set of knee joint prosthetics which function smoothly, continuously, and/or without substantial wear during their life of use.

Similarly, resecting a portion or portions of the proximal tibia can provide a location for placement and/or attachment of a femoral knee joint prosthetic ("proximal tibial resection"). The orientation of a cutting block, and/or cutting plane or planes, can be pre-operatively determined in order to provide a desired fit and/or orientation for the tibial knee joint prosthetic. Properly orientating the cutting plane or planes along the proximal tibia can facilitate alignment of the tibial knee joint prosthetic with the femoral knee joint prosthetic. This alignment can create a set of knee joint prosthetics which function smoothly, continuously, and/or without substantial wear during their life of use.

Joint replacement procedures described above often use a system or systems of surgical tools and devices, including but not limited to cutting guides (e.g. cutting blocks) and surgical guides, to make surgical cuts along a portion or portions of the patient's bone. Current systems and methods often use expensive, complex, bulky, and/or massive computer navigation systems which require a computer or computers, as well as three dimensional imaging, to track a spatial location and/or movement of a surgical instrument or landmark in the human body. These systems are used generally to assist a user to determine where in space a tool or landmark is located, and often require extensive training, cost, and room.

Where such complex and costly system are not used, simple methods are used, such "eyeballing" the alignment of rods with anatomical features, such as leg bones. These simple methods are not sufficiently accurate to reliably align and place implant components and the bones to which such components are attached.

Accordingly, there is a lack of devices, systems and methods that can be used to accurately position components of prosthetic joints without overly complicating the procedures, crowding the medical personnel, and/or burdening the physician of health-care facility with the great cost of complex navigation systems.

During conventional knee arthroplasty, the surgeon often visually aligns the various components required for the femoral and tibial implants.

SUMMARY OF THE INVENTION

In one embodiment, a system is provided for cutting a tibia of a leg of a patient in a uni-condylar procedure. The system includes a guide pin and a sagittal saw guide. The guide pin has a first end configured to be embedded in a distal aspect of a femur and a second end configured to protrude from the femur when the first end is so placed. The sagittal saw guide has a first portion configured to couple with the second portion of the guide pin and a second portion comprising a saw registration feature. Wherein when the first portion of the sagittal saw guide is coupled with the second portion of the guide pin, the second portion of the sagittal saw guide projects distally away from the guide pin to position the saw registration feature over the tibia in a generally sagittal plane.

In another embodiment, a method of cutting a tibia of a leg of a patient in a uni-condylar procedure is provided. The mechanical axis of a femur is located based on output from at least one inertial sensor coupled with the leg. A pin is placed in the femur at an orientation corresponding to the mechanical axis of the femur based on output from at least one inertial sensor. A sagittal saw guide is coupled with the pin such that a saw registration feature is disposed over the tibia in a generally sagittal plane. The tibia is resected along the saw registration feature. Whereby the sagittal resection is made based on the orientation of the mechanical axis of the femur.

In another embodiment, a system for preparing a femur for a femoral cutting block is provided. The system includes a first guide and a second guide. The first guide has a first portion configured to contact a posterior condyle surface and a second portion extending away from the first portion. The second portion is configured to be disposed adjacent to a resected distal femoral surface. The second portion has a drill guide feature spaced from the first portion a distance to provide a mounting position for a femoral cutting block. The second guide has a first portion having a spike member and a second portion extending away from the first portion. The second portion comprises a drill guide feature. The second guide has a linear structure configured to be aligned with a tibial plateau. Whereby the system enables the formation of a plurality of holes for mounting a femoral cutting block to the femur.

In another embodiment, a method of preparing a femur for a femoral cutting block is provided. Resection planes are formed on a distal portion of a femur and a proximal portion of a tibia. A first portion of a first guide is contacted with a posterior condyle of the femur. A second portion of the first guide is positioned over the resection plane of the femur. A first hole is formed in the femur extending superiorly (e.g., toward the hip joint) from the resection plane of the femur through the second portion of the first guide. A first portion of a second guide is coupled with the first hole. A second portion of the second guide is positioned such that a feature of the second guide is aligned with the resection plane of the tibia. A second hole is formed in the femur extending superiorly (e.g., toward the hip joint) from the resection plane of the femur through the second portion of the second guide.

In another embodiment, a system is provided for setting tibial implant rotation. The system includes at least one orientation device and a plurality of tibial trial components. The orientation device(s) is or are configured to be coupled with one or both of a femur and a tibia. Each of the tibial trial components of the plurality is configured to be placed between the tibia and the femur. The system also includes a processor configured to perform one or more of the following functions:
 (i) gathering measurements from one or more inertial sensors of the orientation device(s);
 (ii) performing calculations to convert the measurements from the inertial sensors to tibio-femoral kinematic information;
 (iii) comparing the tibio-femoral kinematic information to target values of tibio-femoral kinematics; and
 (iv) transmitting user output corresponding to one or both of the tibio-femoral kinematic information and the target vales.

In another embodiment, a method for setting tibial implant rotation is provided. In the method, at least one inertial sensor is coupled with at least one of a tibia and a femur of a leg of a patient. An implant is positioned on a resected surface of the tibia of the patient. The leg is moved to position the tibia in a plurality of positions differing in flexion, axial rotation, and/or varus-valgus relative to the femur. Values based on output of the sensors indicative of tibio-femoral kinematics are compared with tibio-femoral kinematic target values for one or more of flexion, axial rotation, and/or varus-valgus.

DETAILED DESCRIPTION OF THE PREFERRED EMBODIMENT

To overcome the problems described above, the certain embodiments of the present invention include devices and/or methods to assist in distal femur resection and proximal tibial resection during knee arthroplasty.

1. Devices for Positioning and Orienting Femoral Cutting Block

The rotation of the femoral implant in total knee arthroplasty (TKA) is set by the placement of the 4-in-1 femoral cutting block, a standard component of the knee system's instrument set. This cutting block is used to guide the creation of the anterior, posterior, anterior chamfer, and posterior chamfer resections. The cutting block usually includes either two fixed spikes, or two holes for bone pins, which are used to secure it to the femur after the distal resection has been completed. Drilling or marking two holes for these features orients and locates the cutting block. The locations of these holes are typically defined by a drill guide device which the surgeon visually aligns with anatomical landmarks on the femur, but which does not account for the mechanical alignment of the femur with the tibia. A drill guide that references the tibia may improve implant function.

Figure 1:
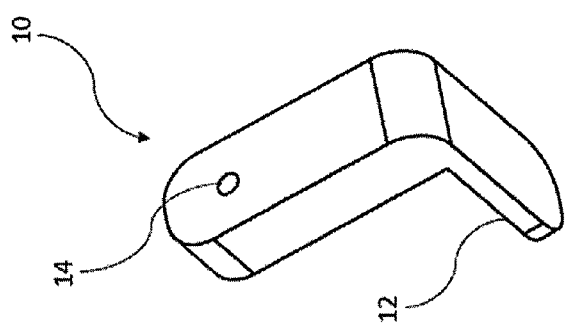
FIG. 1 shows a perspective view of an anterior-posterior positioning guide of one embodiment of the present invention.
Figure 2:
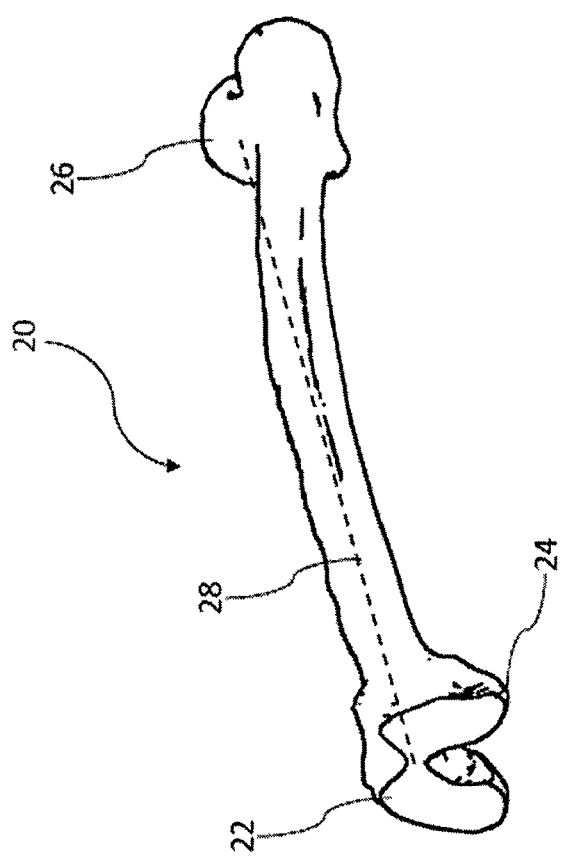
FIG. 2 shows a perspective view of a human femur.
Figure 3:
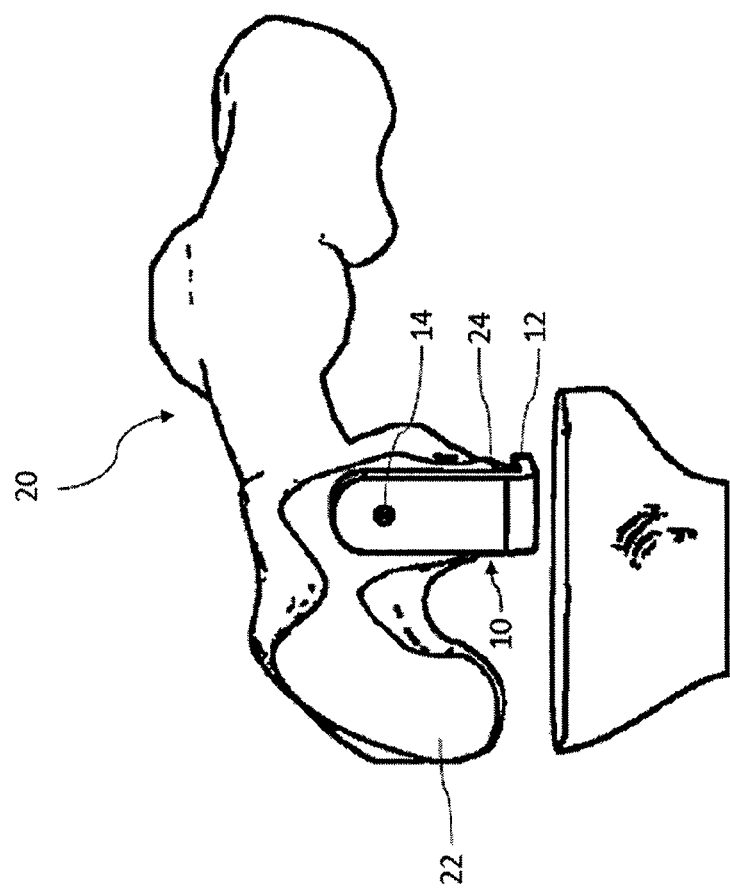
FIG. 3 shows a perspective view of the positioning guide shown in FIG. 1 attached to the femur shown in FIG. 2, with a tibia in an anatomically correct relative location.

Following completion of the tibial resection 41 and the distal femoral resection 22, an AP (anterior-posterior) positioning guide 10 is placed on the distal surface 22 of the femur 20. Referring to FIGS. 1-3, this instrument includes a paddle 12 to reference either the medial or the lateral posterior condyle 24, and a hole 14 to position a drill at a fixed distance anterior to the paddle 12. The distance from the paddle 12 to the hole 14 is determined by the implant system's 4-in-1 cutting block dimensions: The distance is equal to the distance from the posterior cutting slot to the cutting block spike, plus the posterior thickness of the femoral implant. The surgeon drills a hole in the femur 20 through the AP positioning guide 10.

Figure 4:
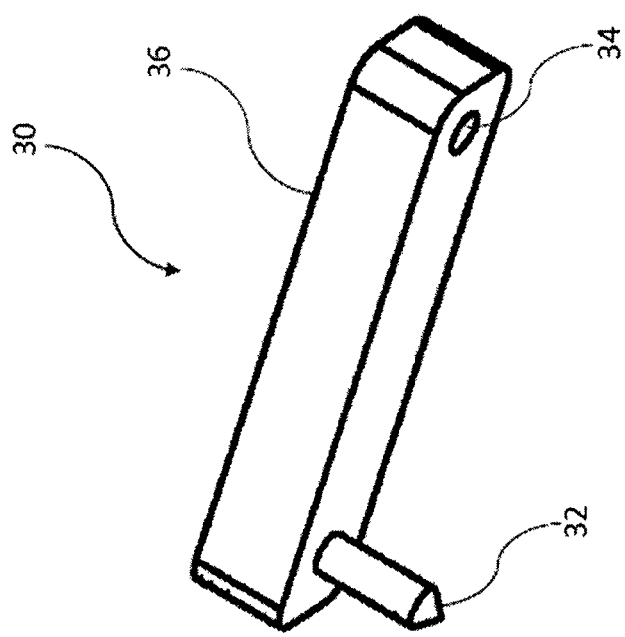
FIG. 4 shows a perspective view of a drill guide of one embodiment of the present invention.
Figure 5:
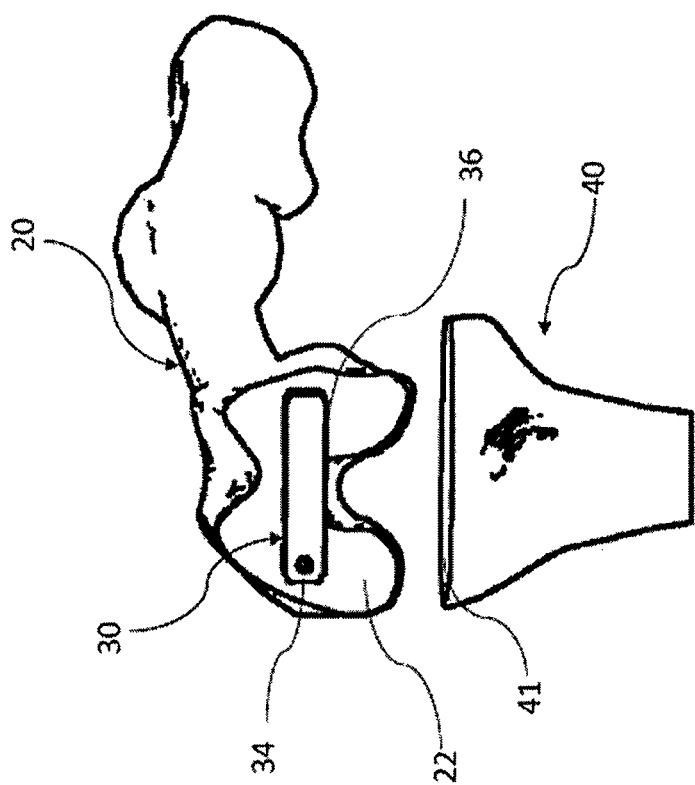
FIG. 5 shows a perspective view the drill guide shown in FIG. 4 positioned on the femur and tibia shown in FIG. 3.

Now referring to FIGS. 4-5, a spike 32 on one end of a drill guide 30 is placed in the hole in the distal femur 22. The drill guide 30 is rotated around the spike 32 until its edge 36 is parallel to the tibial resection 41, then a second hole is drilled into the femur 20 through the hole 34 in the drill guide 30. The drill guide 30 is configured to space the two holes at the correct distance to accommodate the 4-in-1 cutting block's mounting pins.

Preferably, the technique described would include the use of some commonly-used tensioning instrument (e.g., laminar spreader) to hold the femur 20 in the correct rotational alignment with the tibia 40 while aligning the drill guide 30 with the tibial resection 41.

2. Devices for Setting Rotation of Sagittal Resection for UKA Tibial Implant

In unicompartmental knee arthroplasty (UKA), the tibial implant replaces only the (usually) medial compartment of the tibia. Accordingly, two tibial resections are performed, one in a transverse plane, and one in a sagittal plane. This sagittal resection both defines the medial-lateral position of the implant, and sets the rotation of the implant relative to the tibia. The rotation of this sagittal resection is typically visually aligned according to surgeon preference and experience. This visual alignment does not account for the mechanical alignment of the femur with the tibia. A cutting guide that references the femur may improve implant function.

Figure 6:
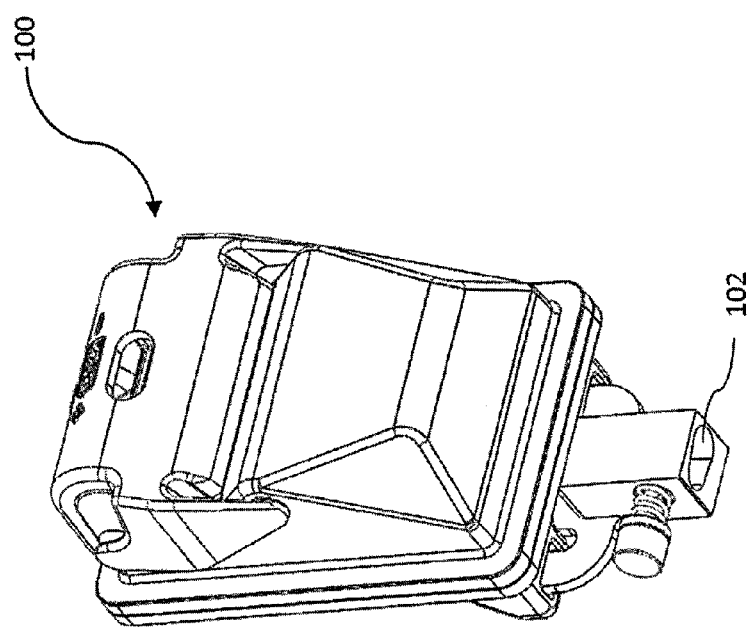
FIG. 6 shows a perspective view of a reference device of one embodiment of the present invention.
Figure 7:
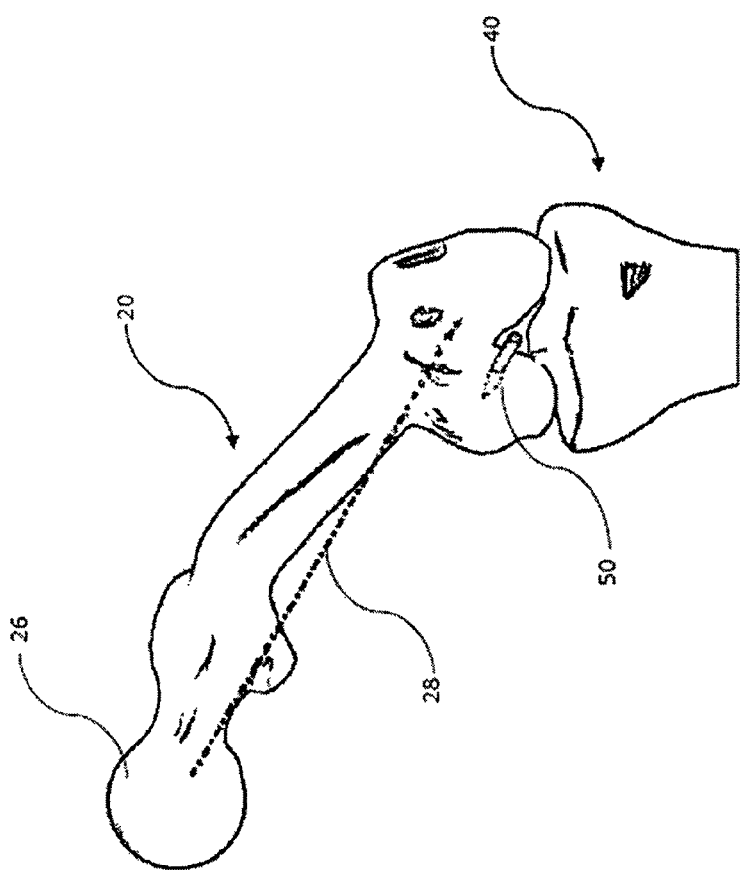
FIG. 7 shows a perspective view of a femur, tibia, and a guide pin of one embodiment of the present invention.

Referring to FIGS. 6-7, the mechanical axis 28 of the femur 20 is calculated by a reference device 100, which contains accelerometers and gyroscopes to sense its angular orientation and rate, and which is fixed to the femur 20. The reference device 100 incorporates generally the same components and basic measurement functions as described in U.S. Pat. No. 8,118,815 for its reference device (e.g., 16), and may be identical to this device. A surgical orientation device 200, such as the device shown in FIG. 8, communicates with the reference device and displays the angle of the surgical orientation device relative to the calculated mechanical axis 28. The surgical orientation device 200 incorporates generally the same components and basic measurement functions as described in U.S. Pat. No. 8,118,815 for its surgical orientation device (e.g., 14). U.S. Pat. No. 8,118,815 is hereby incorporated by reference in its entirety.

With reference to FIG. 7, a guide pin 50 is then placed in the distal femur 20, with its axis parallel to the mechanical axis 28 of the femur 20, as determined by the reference device 100. Alternatively, the guide pin 50 may be placed to align its axis toward the femoral head 26. The surgical orientation device 200 may be used to guide placement of the pin 50.

This guide pin 50 is used to position a cutting block 60, which references the pin 50 by a mating hole 62 in the cutting block 60, and which also includes a cutting slot 64 for the sagittal resection on the tibia 40. The cutting slot 64 guides the saw during resection of the tibia 40.

Optionally, the cutting block 60 could be configured to allow medial-lateral translation between the guide hole 62 and the cutting slot 64. This would allow the rotation and position of the sagittal resection to be set independently. Also optionally, the cutting block 60 could include a second cutting slot oriented in a transverse plane. This second cutting slot would provide guidance for the saw during resection of the tibia 40 in the transverse plane.

As an alternative method, the surgical orientation device 200 could be mounted on the cutting block 60 and used to align it relative to the mechanical axis 26 without using the guide pin 50. The surgical orientation device 200 would display real-time orientation to the user during placement and pinning of the cutting block 60. If the cutting block 60 included a second (transverse) cutting slot as described above, the angular display from the surgical orientation device could also be used to align this second slot relative to the mechanical axis of the tibia 40.

3. Methods for Setting the Rotation of the Tibial Implant by Kinematic Measurements The rotation of the tibial implant in TKA is set following completion of the tibial resection. The tibial implant can be rotated in any direction on the resected tibial surface. Final rotation of the implant is typically determined by the surgeon by one or more of three methods: 1) visually maximizing coverage of the resected surface in an attempt to place the implant as nearly as possible on the outer rim of the bone; 2) visually aligning the anterior-posterior (AP) axis of the implant with an anatomic landmark such as the tibial tubercle; 3) allowing the implant to rotate freely, then fixing the tibial implant in the rotational alignment dictated by contact with the femur with the knee in full extension (hereinafter referred to as "traditional methods"). A more precise and/or quantifiable alignment method is likely to improve implant performance and patient satisfaction. The present invention provides, in certain embodiments, such more precise and/or quantifiable alignment methods to improve implant performance and patient satisfaction.

Figure 10:
FIG. 10 shows a top view of a tibia including contact point lines.

The present invention provides, in one embodiment, a method for setting the rotation of the tibial implant by kinematic measurements based upon femur-tibia contact points. In this method of the present invention and referring to FIG. 7, the femur 20 contacts the tibia 40 at two points: one medial, and one lateral. As the knee flexes through its range of motion, the location of these contact points on the tibia 40 are recorded. At any instantaneous flexion angle, a line connecting the two contact points can be constructed, as shown in FIG. 10. Lines 42-45 represent the lines connecting the medial and lateral contact points throughout the range of motion, from line 42 at full extension, to line 45 at full flexion. At any flexion angle, a line 46-49 perpendicular to the instantaneous contact point lines 42-45 defines an AP axis that can be used as a reference for tibial component alignment.

The contact points are identified using one of several art-disclosed methods and devices including, without limitations, (i) pressure-sensitive film (e.g., "Prescale" film manufactured by Fujifilm® Corp.); and (ii) use of knee implant measurement devices such as those described by D'Lima et al., "Tibial Forces Measured In Vivo After Total Knee Arthroplasty," Journal of Arthroplasty p. 255-262 (Vol. 21 No. 2 Feb. 2006), which contain load cells able to measure contact forces. Once the contact points and connecting line 42-45 are identified, the AP axis of the tibial component is aligned with any one of the perpendicular AP axes 46-49 chosen according to surgeon preference. Alternatively, an AP axis could be calculated as an average of all axes throughout the range of motion, or could be a weighted average with greater weight given to a specific range of flexion angles.

The present invention also provides, in one embodiment, a method for setting the rotation of the tibial implant by kinematic measurements based on inertial measurement of tibio-femoral kinematics. In this method of the present invention and referring to FIGS. 6-7, one reference device 100 is securely attached to each of the femur 20 and tibia 40. The reference device 100 attached to the femur 20 is aligned approximately with the femoral mechanical axis 28. The reference devices are preferably mounted in a manner which allows normal function of the patella to reproduce normal knee kinematics. A medialized attachment is preferred on both the tibia 40 and femur 20 to better accommodate the typical surgical exposure. Optionally, the orientation of the mechanical axis 28 is calculated relative to the reference device 100 following the method described in U.S. Pat. No. 8,118,815. If desired, this offset angle can be applied to the reference device 100 for greater measurement accuracy.

In order to establish the characteristics of the knee joint prior to resection, the surgeon brings the knee into full extension and moves the leg through a short arc of motion, pivoting about the femoral head 26 in all directions and rotating about the long axis of the leg. During this motion, the two references devices 100, stationary relative to each other, perform a "transfer alignment" to calculate the relative misalignment between the two reference devices 100, allowing the orientation of the tibial device to be established in the frame of reference of the femoral device.

Figure 8:
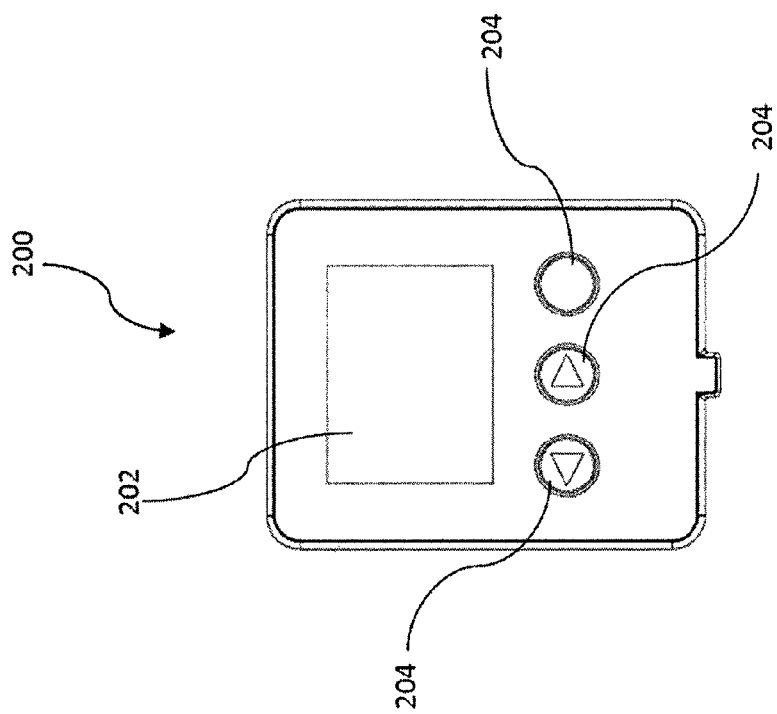
FIG. 8 shows a front view of a surgical orientation device of one embodiment of the present invention.
Figure 9:
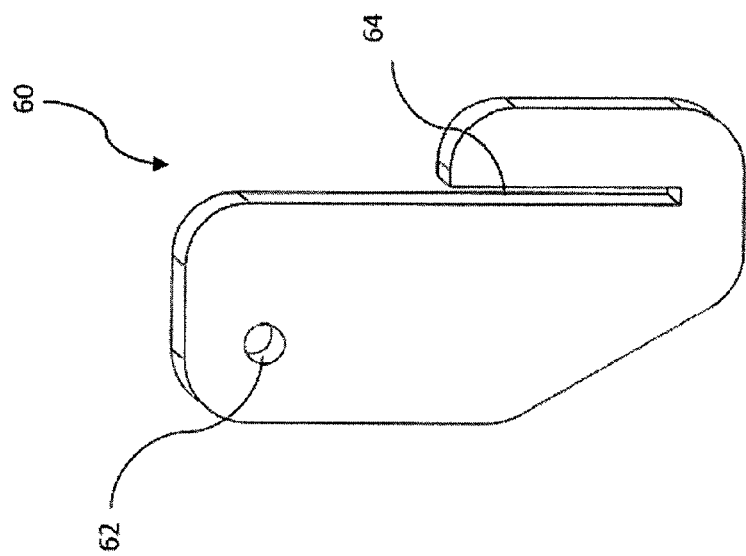
FIG. 9 shows a front view of a cutting block of one embodiment of the present invention.

The knee is then taken through a range of motion. Relative rotations between the tibia 40 and femur 20 are measured by comparing the angular changes recorded by their respective reference devices 100 throughout the range of motion. These rotations are resolved into three directions corresponding to the flexion, axial rotation, and varus/valgus directions. The rotations are transmitted to the surgical orientation device 200 as shown in FIG. 8, which graphically displays to the user plots of axial rotation and varus/valgus rotation vs. flexion angle. The surgical orientation device 200 may also display numerical values for the rotation angle at various flexion angles of interest, such as 90 degrees or 120 degrees.

During trial reduction, the surgeon repeats the above procedure. The surgical orientation device 200 then displays the aforementioned kinematic data graphically and superimposes the trial curves upon the pre-operative curves and/or calculates the appropriate amount by which the tibial component should be rotated about the tibial axis in order to best approximate the pre-operative curves. An optimization algorithm can be employed for this purpose.

The surgeon then adjusts the rotational alignment of the tibial implant and repeats the measurements above until the rotations of the tibia 40 relative to the femur 20 match the target rotations. These target rotations may be based on published averages for healthy knees, or on kinematic measurements taken from the same patient prior to resection.

As an additional optional step, the surgeon applies alternating varus and valgus torque to the knee in order to gauge the tibio-femoral rotation allowed in each direction. This varus or valgus rotation is displayed on the surgical orientation device 200, supplementing the traditional visual estimation of knee laxity in the varus/valgus direction. This rotation information provides a means to quantitatively compare the varus and valgus laxity, towards the traditional goal of balancing the two by means of soft tissue releases. This measurement can be used to quantify the laxity of the knee joint in full extension, 90 degrees flexion or any other angle to which the knee can be flexed.

The present invention further provides, in one embodiment, a method for setting the rotation of the tibial implant by kinematic measurements using load cells to measure contract forces between the tibial implant and the femoral implant. In this method of the present invention, the trial tibial implant is fitted with load cells able to measure contact forces between the tibial implant and the femoral implant. Such devices have been developed previously, and function similarly to the instrumented implant described by D'Lima et al., "Tibial Forces Measured In Vivo After Total Knee Arthroplasty," Journal of Arthroplasty p. 255-262 (Vol. 21 No. 2 Feb. 2006).

This instrumented trial tibial component is fixed to the tibia 40 in a rotation determined by the traditional methods described above. As the knee is taken through a range of motion, the trial component transmits the measured contact forces to a surgical orientation device 200, which stores and displays the force data, either as a peak force number, a force vs. flexion angle history, or both. The surgeon then iteratively adjusts the alignment of the trial tibial component and repeats the force measurement steps. The tibial component alignment that provides the best fit with the soft tissue kinematic envelope will be identified as the configuration that produces the minimum tibio-femoral contact force.

The present invention also provides, in one embodiment, a method for setting the rotation of the tibial implant by kinematic measurements based upon measurement of tibial interface torque. In this method of the present invention, the trial tibial implant is fitted with a torque transducer able to measure axial torque between the tibial articular surface and the tibia 40. Such devices have been previously demonstrated, such as the instrumented implants described by Heinlein et al. in the Journal of Biomechanics (Vol. 41 No. 10). For the purposes of the present invention, the torque is measured around an axis approximately parallel to the long axis of the tibia 40. This instrumented trial tibial component is fixed to the tibia 40 in a rotation determined by the traditional methods described above. As the knee is taken through a range of motion, the trial component transmits the measured torque to a surgical orientation device 200, which stores and displays the torque data, either as a peak torque number, a torque vs. flexion angle history, or both. The surgeon then iteratively adjusts the alignment of the trial tibial component and repeats the torque measurement steps. The tibial component alignment that provides the best fit with the soft tissue kinematic envelope will be identified as the configuration that produces the minimum axial torque.

Many other variations than those described herein and/or incorporated by reference will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein or incorporated herein by reference can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described or incorporated functionality can be implemented in varying ways for each particular application, but such implementation decisions should not be interpreted as causing a departure from the scope of the disclosure.

The various illustrative logical blocks and modules described in connection with the embodiments disclosed herein or incorporated by reference can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A method for setting tibial implant rotation, comprising: coupling at least one inertial sensor with at least one of a tibia and a femur of a leg of a patient; positioning an implant on a resected surface of the tibia of the patient; moving the leg to position the tibia in a plurality of positions differing in flexion, axial rotation, and/or varus-valgus relative to the femur; comparing values based on output of the at least one inertial sensor indicative of tibio-femoral kinematics with tibio-femoral kinematic target values for one or more of flexion, axial rotation, and/or varus-valgus; and quantitatively comparing the varus and valgus laxity.

2. The method of claim 1, wherein comparing values further comprises comparing values based on output of the at least one inertial sensor with target values for a healthy knee.

3. The method of claim 1, wherein comparing values further comprises comparing values based on output of the at least one inertial sensor with one or more patient-specific values.

4. The method of claim 3, further comprising recording patient-specific values of tibio-femoral kinematics of the knee prior to resecting the tibia.

5. The method of claim 3, further comprising recording patient-specific values of tibio-femoral kinematics of a contralateral knee prior to resecting the tibia.

6. The method of claim 1, further comprising adjusting the rotation of the knee and repeating the moving step and the comparing step.

7. The method of claim 1, further comprising balancing the varus and valgus laxity by soft tissue releases.

8. The method of claim 1, wherein coupling the at least one inertial sensor comprises coupling a first device with the femur and a second device with the tibia.

9. The method of claim 1, wherein quantitatively comparing the varus and valgus laxity comprises applying alternating varus and valgus torque in order to gauge the tibio-femoral rotation allowed in each direction.

10. A method for setting tibial implant rotation, comprising: coupling at least one inertial sensor with at least one of a tibia and a femur of a leg of a patient; positioning an implant between the tibia and the femur; moving the leg to gather a measurement from the at least one inertial sensor; comparing information based on the measurement with a target value of tibio-femoral kinematics; and quantitatively comparing the varus and valgus laxity.

11. The method of claim 10, wherein comparing information further comprises comparing information based on output of the at least one inertial sensor with target values for a healthy knee.

12. The method of claim 10, wherein comparing information further comprises comparing information based on output of the at least one inertial sensor with one or more patient-specific values.

13. The method of claim 10, further comprising balancing the varus and valgus laxity by soft tissue releases.

14. The method of claim 10, wherein coupling the at least one inertial sensor comprises coupling a first device with the femur and a second device with the tibia.

15. The method of claim 10, wherein quantitatively comparing the varus and valgus laxity comprises applying alternating varus and valgus torque in order to gauge the tibio-femoral rotation allowed in each direction.

16. The method of claim 10, further comprising performing calculations to convert the measurements from the at least one inertial sensor to tibio-femoral kinematic information, wherein comparing information based on the measurement comprises comparing the tibio-femoral kinematic information to the target values of tibio-femoral kinematics.

17. A method for setting tibial implant rotation, comprising: coupling at least one inertial sensor with at least one of a tibia and a femur of a leg of a patient; moving the leg to gather one or more measurements from the at least one inertial sensor in one or more positions differing in flexion, axial rotation, and/or varus-valgus relative to the femur; comparing a value based on the one or more measurements indicative of tibio-femoral kinematics with a tibio-femoral kinematic target value for one or more of flexion, axial rotation, and/or varus-valgus; and quantitatively comparing the varus and valgus laxity.

18. The method of claim 17, further comprising positioning an implant between the tibia and the femur.

19. The method of claim 17, wherein quantitatively comparing the varus and valgus laxity comprises applying alternating varus and valgus torque in order to gauge the tibio-femoral rotation allowed in each direction.

* * * * *